(12) United States Patent
Johannaber

(10) Patent No.: US 9,232,951 B2
(45) Date of Patent: Jan. 12, 2016

(54) KNEE ARTHROPLASTY APPARATUS AND METHOD

(75) Inventor: Kenneth Dale Johannaber, Reno, NV (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 1253 days.

(21) Appl. No.: 13/009,148

(22) Filed: Jan. 19, 2011

(65) Prior Publication Data

US 2012/0184961 A1    Jul. 19, 2012

(51) Int. Cl.
| | |
|---|---|
| *A61B 17/58* | (2006.01) |
| *A61B 17/60* | (2006.01) |
| *A61F 2/00* | (2006.01) |
| *A61B 17/15* | (2006.01) |
| *A61B 17/17* | (2006.01) |
| *A61B 19/00* | (2006.01) |

(52) U.S. Cl.
CPC .......... *A61B 17/157* (2013.01); *A61B 17/1703* (2013.01); *A61B 2019/461* (2013.01)

(58) Field of Classification Search
CPC .......... A61B 17/1675; A61B 17/1764; A61B 17/154
USPC .......................................................... 606/88
See application file for complete search history.

(56) References Cited

U.S. PATENT DOCUMENTS

| | | |
|---|---|---|
| 2005/0222573 A1 | 10/2005 | Branch et al. |
| 2007/0219559 A1 | 9/2007 | Heavener et al. |
| 2008/0119891 A1* | 5/2008 | Miles et al. .................. 606/213 |
| 2009/0234360 A1 | 9/2009 | Alexander |
| 2010/0069911 A1 | 3/2010 | Borja et al. |
| 2010/0198275 A1 | 8/2010 | Chana et al. |

OTHER PUBLICATIONS

"International Application Serial No. PCT/US2011/023189, International Preliminary Report on Patentability mailed Aug. 1, 2013", 7 pgs.
"International Application Serial No. PCT/US2011/023189, International Search Report mailed Feb. 17, 2012", 4 pgs.

* cited by examiner

*Primary Examiner* — David Isabella
*Assistant Examiner* — Christine Nelson
(74) *Attorney, Agent, or Firm* — Schwegman Lundberg & Woessner, P.A.

(57) ABSTRACT

A method for aligning a bone cutting guide on a tibia may involve coupling a cutting guide alignment device and an attached cutting guide with a tibia, adjusting the alignment device in a varus/valgus orientation, adjusting the alignment device in an anterior/posterior orientation, attaching the cutting guide to the tibia, and removing the alignment device from the cutting guide, leaving the cutting guide attached to the tibia. The adjustments to the alignment device may be made according to vertically and horizontally oriented laser lights emitted from the alignment device. As the alignment device is adjusted, the bone cutting guide attached to the alignment device changes position relative to the tibia.

24 Claims, 9 Drawing Sheets

KNEE ARTHROPLASTY APPARATUS AND METHOD

BACKGROUND OF THE INVENTION

Embodiments of the invention relate to medical/surgical devices, systems and methods. More specifically, embodiments of the invention relate to devices, systems and methods for enhancing a knee surgery procedure.

Approximately 550,000 total knee replacement surgeries (also referred to as total knee arthroplasty ("TKA") are performed annually in the U.S. for the treatment of chronic knee pain and dysfunction. As the U.S. and world populations become older and more obese, knee replacement surgery will become even more common, as knee joints endure greater and greater wear and tear from their increased loads and years of stress. Conventional TKA surgery is often very effective but also very invasive and sometimes imprecise, thus leading to less than ideal outcomes.

The knee is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away to allow the femur to directly contact the tibia. This bone-on-bone contact causes significant pain and discomfort. The primary goals of a TKA procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

In a TKA surgery, the surgeon cuts open the knee, flips the patella bone out of the way, cuts bone from the distal end of the femur and from the proximal end of the tibia, and installs new, manmade, prosthetic ends onto the femur and tibia to form a new knee joint. In some TKA procedures, the interior surface of the patella may also be covered with a prosthetic. Cutting open the knee, moving the patella, sawing off bone segments, and implanting the manmade implants is a very invasive, though effective, procedure. Determining how to cut the ends of the femur and tibia to ensure proper alignment and balancing of ligament tension in the new, prosthetic knee joint can be very challenging and often involves more art than science. An artificial knee joint in which the ligament tension is not well balanced endures significantly more wear and tear than one that is properly balanced, and yet, this proper balance is very difficult to achieve. As a consequence, TKA surgery performed on younger patients typically needs to be redone one or more times during the patient's life.

Due to the invasiveness and imprecision of traditional TKA, there is a need for improved techniques and devices in this field. A number of minimally invasive (or "less invasive") TKA techniques, involving smaller incision sizes and reduced trauma to the patient have been developed in an effort to reduce patient recovery time. Some of these minimally invasive techniques, as well as other innovations, have also sought to enhance and/or facilitate TKA by making it more precise and repeatable and thus, ideally, reducing wear and tear on artificial knees and the need for repeat procedures. Improved techniques and devices would also mean enhanced outcomes for all TKA patients, with better functioning of the knee joint and longer useful life of the artificial knee.

One of the greatest challenges in TKA surgery is to properly balance ligament tension, especially in the medial and lateral collateral ligaments, through a full range of motion of the knee. The collateral ligaments, which connect the distal femur and proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may move (or "track") improperly, and the femur and/or tibia may wear unevenly, leading to arthritis and pain. Uneven ligament tension after TKA surgery will typically cause joint instability and poor patellar tracking, limited range of motion, and impaired function of the knee, as well as uneven, increased wear of the prosthetic device, which often necessitates repeat surgery. Thus, it is imperative for the short- and long-term success of a TKA procedure to achieve balanced ligament tension in the knee through a full range of motion.

Balancing ligament tension during TKA surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc during knee flexion. In addition, the femur translates anteriorly and posteriorly as the tibia is being flexed about it, bringing yet another movement variable into the equation. Thus, the ligaments of the knee, along with the femur, tibia and patella, create a truly dynamic bio-mechanism, making ligament tension balancing in TKA surgery extremely challenging. This challenge is even greater in minimally invasive TKA procedures, in which incisions are smaller than those made in "open" TKA surgeries. Additionally, the incision made during minimally invasive TKA surgery is biased to the medial side, leaving the lateral side of specifically the distal femur "closed" to access of front or end loaded surgical instruments One way surgeons try to balance ligament tension during TKA procedures is by cutting one or more ligaments to release tension from one part of the joint ("ligament release"). The disadvantage of ligament release, however, is that once a ligament is cut it cannot be regenerated, and the ligaments of the knee provide much needed stability to the knee joint.

Rather than or in addition to ligament release, the components of a total knee prosthesis may be selected and positioned to balance ligament tension. Since the femoral and tibial components of the knee prosthesis are attached to cut surfaces of the distal femur and proximal tibia respectively, placement and orientation of the femoral and tibial bone cuts are very important for balancing knee ligament tension. As with ligament release however, it is often very challenging to position the femoral and tibial bone cuts and prosthetic components to provide ideal ligament tension through the range of motion. This is due primarily to the complexity of motion about the knee, as described above, and the difficulty of assessing and making the bone cuts during the procedure to achieve desired ligament tension through the full range of motion.

Improved methods and apparatus for facilitating and/or enhancing femoral bone cuts have been described in, for example, U.S. Pat. Nos. 7,578,821 and 7,442,196. The assignee of the present application has also described various embodiments of a method and system for facilitating and/or improving tibial bone cuts in a TKA procedure in U.S. patent application Ser. No. 12/729,222, filed on Mar. 22, 2010, the full disclosure of which is incorporated herein by reference.

To make a tibial cut in a TKA procedure, an orthopedic surgeon typically uses a cutting block or cutting guide temporarily attached to the front of the tibia via a rod that is typically attached to an ankle clamp at the distal end to the tibia (an extramedulary rod) and aligned approximately with the mechanical axis of the anterior surface of the tibia. The cutting block is used to guide a surgical saw blade or rotary tool in making the tibial bone cut. Positioning such a cutting block, therefore, is crucial to forming well-positioned bone cuts for attachment of the tibial and femoral prosthetic components. The tibial cut is the foundation of a TKA, as it affects the spacing, alignment and balance between the tibia and femur when the knee is in flexion (the flexion gap), the spacing, alignment and balance between the tibia and femur when the knee is in extension (the extension gap), and all points of articulation between extension and flexion. Typically, the tibial component of a knee prosthesis is positioned on a flat, horizontal cut surface of the proximal tibia (at a 90 degree "varus/valgus" angle relative to the long axis of the tibia), and the position and orientation of the tibial component typically do not vary greatly from knee to knee. By making a cut on the tibia at 90 degrees to the long axis of the bone, however, a bigger space is created laterally than medially, due to the tibia's natural approximately 3 degrees of varus slope. Furthermore, the "classic" 90-degree tibial bone cut is typically made by the surgeon simply approximating the 90-degree angle. Therefore, the usual cut made to the tibia in TKA is not necessarily ideal and is made by approximation. Thus, improvements to the angle and precision of the tibial cut may improve the ligament balancing and overall result of a TKA procedure.

Therefore, a need exists for improved devices, systems and methods for enhancing TKA surgery and specifically for enhancing and/or facilitating the positioning of one or more tibial bone cuts made during a TKA procedure to accommodate a tibial prosthetic. Ideally, such devices, systems and methods would allow a physician to effectively select an angle at which to make a tibial bone cut and would help the physician more accurately make the cut at the selected angle. Such devices, systems and methods would also ideally be simple to use in conjunction with cutting guides, saw blades or burs, robotic and navigational systems, and/or any other equipment used by a surgeon in a TKA procedure. At least some of these objectives will be met by various embodiments of present invention.

BRIEF SUMMARY OF THE INVENTION

The present invention provides devices, systems and methods for positioning a bone cut on a tibia as part of a TKA or other knee surgery procedure. These devices, systems and methods generally help a physician achieve balancing of ligaments during the knee surgery procedure, thus potentially enhancing the outcome of the procedure and/or reducing wear and tear of an artificial knee joint implanted during the procedure.

In one aspect, a method for positioning a bone cutting guide on a tibia may involve: coupling the bone cutting guide with a cutting guide alignment device; measuring a length of the tibia from approximately a tibial plateau to a centerline of a malleolus of the tibia; adjusting the alignment device according to the length of the tibia; positioning a stylus of the alignment device on a low point of a proximal end of the tibia; contacting the cutting guide with a tibial tubercle of the tibia; driving a first pin through a first opening on the cutting guide into the tibia; adjusting the alignment device to align a cross-shaped laser light emitted from the alignment device approximately with a center of an ankle formed by the distal end of the tibia, wherein adjusting the alignment device moves the cutting guide into an adjusted position; and driving at least a second pin through a second opening on the cutting guide into the tibia to secure the cutting guide to the tibia in the adjusted position. In one embodiment, the method may further involve driving at least a third pin through a third opening on the cutting guide into the tibia.

In one embodiment, coupling the bone cutting device with the alignment device may involve pressing a guide release button on the alignment device, sliding the cutting guide onto a post on the alignment device, and releasing the guide release button to lock the cutting guide onto the alignment device. Some embodiments may further involve, after driving the second pin, pressing the guide release button and removing the alignment device from the cutting guide, leaving the cutting guide attached to the tibia. In some embodiments, adjusting the alignment device according to the length of the tibia comprises adjusting a laser emitting member to direct the emitted laser light along the length of the tibia. In some embodiments, aligning the emitted laser light may involve aligning a vertically oriented laser light along approximately a midline of the tibia and aligning a horizontally oriented laser light along approximately a centerline of the ankle. In many cases, the method may also include removing the alignment device from the cutting guide and cutting the tibia with a bone saw, using the attached cutting guide.

In another aspect, a method for aligning a bone cutting guide on a tibia may involve: coupling a cutting guide alignment device and an attached cutting guide with a tibia; adjusting the alignment device in a varus/valgus orientation, using a vertically oriented laser light emitted from the alignment device; adjusting the alignment device in an anterior/posterior orientation, using a horizontally oriented laser light emitted from the alignment device; attaching the cutting guide to the tibia; and removing the alignment device from the cutting guide, leaving the cutting guide attached to the tibia. In this embodiment, adjusting the alignment device moves the cutting guide relative to the tibia.

In one embodiment, adjusting the alignment device in the varus/valgus direction may involve rotating a handle of the device to the left and/or right, and adjusting the alignment device in the anterior/posterior direction may involve rotating the handle toward and/or away from the tibia. The attached cutting guide, according to one embodiment, is configured to provide approximately a three degree (3°) tibial slope when attached according to the adjustments to the alignment device. In general, after removing the alignment device from the cutting guide, a bone saw may be used to make a cut on the tibia, using the cutting guide.

In another aspect, a device for positioning a bone cut on a tibia may include: a handle; an adjustable laser light emitter coupled with the handle and configured to be adjustable according to a length of the tibia; a cutting guide attachment member coupled with the handle for removably attaching a cutting guide to the handle; and a proximal tibia contacting member coupled with the handle for contacting a low point on a proximal end of the tibia as a reference point for the device. In one embodiment, the handle may include a horizontal portion having a slot along which the laser light emitter slides and a cutting guide release actuator for releasing the cutting guide from the cutting guide attachment member. In some embodiments, the cutting guide attachment member may include a locking mechanism for locking the cutting guide to the handle until the release actuator is activated. In some embodiments, the horizontal portion may include numbers denoting different lengths of tibias to facilitate adjustment of the laser light emitter. The proximal tibia contacting member of the device may comprise, for example, a stylus. In some embodiments, the device may further include a left bone cutting guide for use in cutting a left tibia and a right bone cutting guide for use in cutting a right tibia.

In another aspect, a system for positioning a bone cut on a tibia may include: a handle; an adjustable laser light emitter coupled with the handle and configured to be adjustable according to a length of the tibia; a cutting guide attachment member coupled with the handle; a proximal tibia contacting member coupled with the handle for contacting a low point on a proximal end of the tibia as a reference point for the device; and at least one bone cutting guide removably attachable to the handle via the cutting guide attachment member. In one embodiment, the handle may include a horizontal portion having a slot along which the laser light emitter slides and a cutting guide release actuator for releasing the cutting guide from the cutting guide attachment member. In some embodiments, the system may include a left bone cutting guide for use in cutting a left tibia and a right bone cutting guide for use in cutting a right tibia. The system may also optionally include a tibia measuring device for measuring a length of the tibia.

For a further understanding of the nature and advantages of the invention, reference should be made to the following description taken in conjunction with the accompanying figures. Each of the figures is provided for the purpose of illustration and description only, however, and is not intended to limit the scope of the embodiments of the present invention.

DETAILED DESCRIPTION OF THE INVENTION

The devices, systems and methods described below may be used in various embodiments to enhance and/or facilitate a total knee arthroplasty (TKA) procedure, a partial knee arthroplasty procedure, or any other suitable knee surgery procedure in which one or more cuts are made on a tibia, typically a proximal end of a tibia. Generally, the embodiments described herein provide a means for positioning a bone cut on a tibia. Although the following description may frequently refer to TKA procedures, the described embodiments may also be used for partial knee arthroplasty procedures or other knee procedures in which tibial bone cuts are made.

Figure 1:
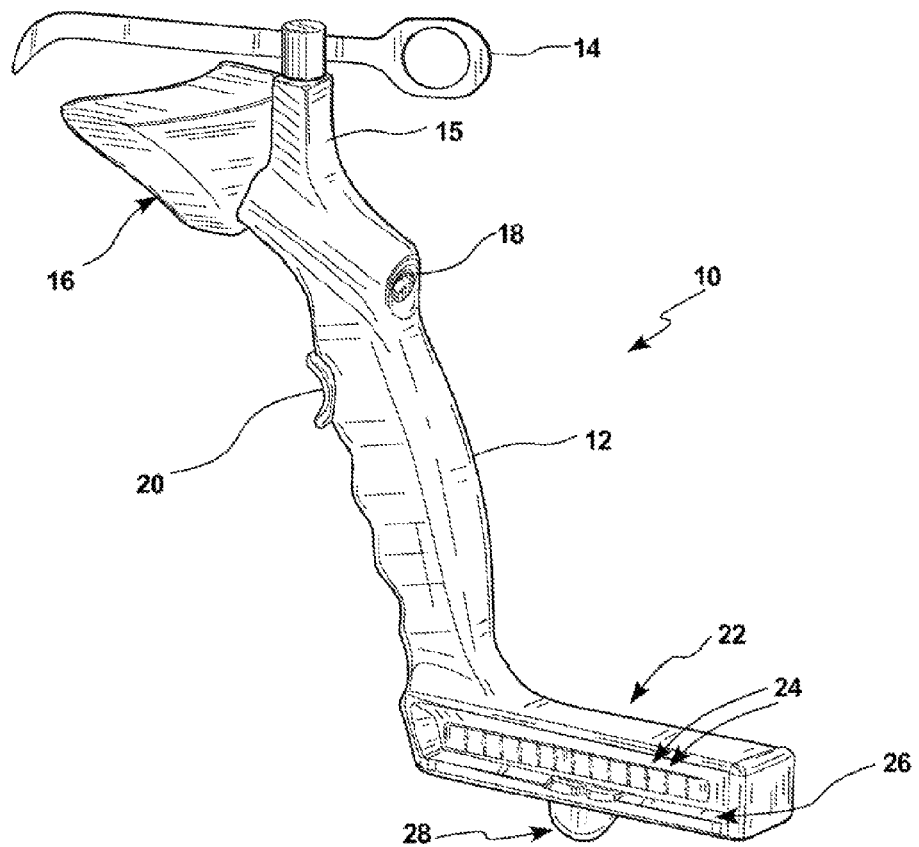
FIG. 1 is a perspective view of a tibial bone cut alignment system, according to one embodiment.

Referring to FIG. 1, one embodiment of a tibal bone cut alignment system 10 is shown. Throughout this application, system 10 may be referred to as a "bone cut alignment system," "bone cut positioning system," "bone cutting guide alignment system," or other similar terms. Unless otherwise specified, these descriptive phrases for system 10 are synonymous. In the embodiment show, system 10 includes a handle 12 having a number of features and coupled with a bone cutting guide 16. The features of handle 12 include a stylus 14 for contacting a proximal surface of a tibia, a slot 15 through which pins are advanced to attach cutting guide 16 to a tibia, a guide release button 18 for releasing cutting guide 16 from handle 12, a horizontal extension 22 with a slot 26, measurement indicators 24, and a laser light emitter 28 slidably positioned in slot 26, and a trigger switch 20 to activate laser light emitter 28.

In various embodiments, system 10 may be provided with one or more bone cutting guides 16, such as a left-sided guide and a right-sided guide. In other embodiments, handle 12 may be provided alone. In either case, handle 12 may be compatible with any of a number of available cutting guides.

Figure 2:
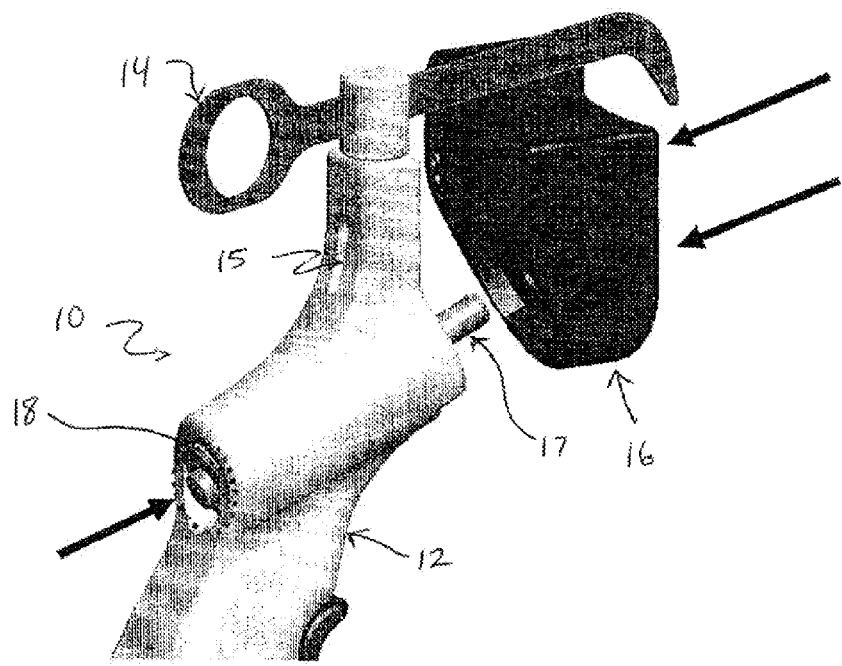
FIG. 2 is a close-up perspective view of a portion of the tibial bone cut alignment system from FIG. 1.

Referring now to FIG. 2, system 10 and one embodiment of a method for using it will be described in further detail. As a first step, cutting guide 16 may be attached to handle 12 via a cutting guide attachment member 17, such as a post with one or more locking elements. In the embodiment shown, guide release button 18 may be depressed to allow cutting guide 16 to be mounted onto cutting guide attachment member 17. When guide release button 18 is subsequently released, locking elements on attachment member 17 are activated and lock cutting guide 16 onto handle 12. When cutting guide 16 is later attached to a tibia, button 18 may be depressed again to allow cutting guide 16 to be released from handle 12, thus remaining attached to the tibia. In alternative embodiments, any suitable alternative attachment mechanism may be used for attaching bone cutting guide 16 to handle 12, such as but not limited to a magnetic attachment, multiple posts, screw(s), clasp(s) or the like.

Figure 3:
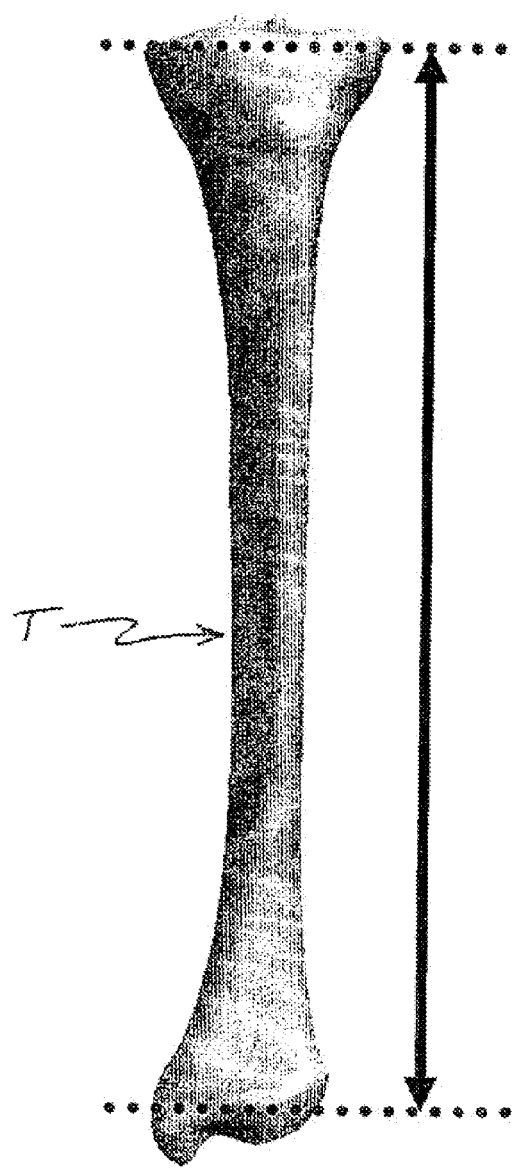
FIG. 3 is a front view of a tibia, demonstrating a measurement of the length of the tibia.

Turning to FIG. 3, a next step of the method may involve measuring the length of a tibia T. In some embodiments, system 10 may include a tibia length measuring device, such as a simple tape measure. Typically, though not necessarily, the length of the tibia T is measured from the low point on the tibial plateau (PT) (proximally) to the centerline of the lateral malleolus (distally), as shown by the dotted lines and two-headed arrow in FIG. 3.

Figure 4:
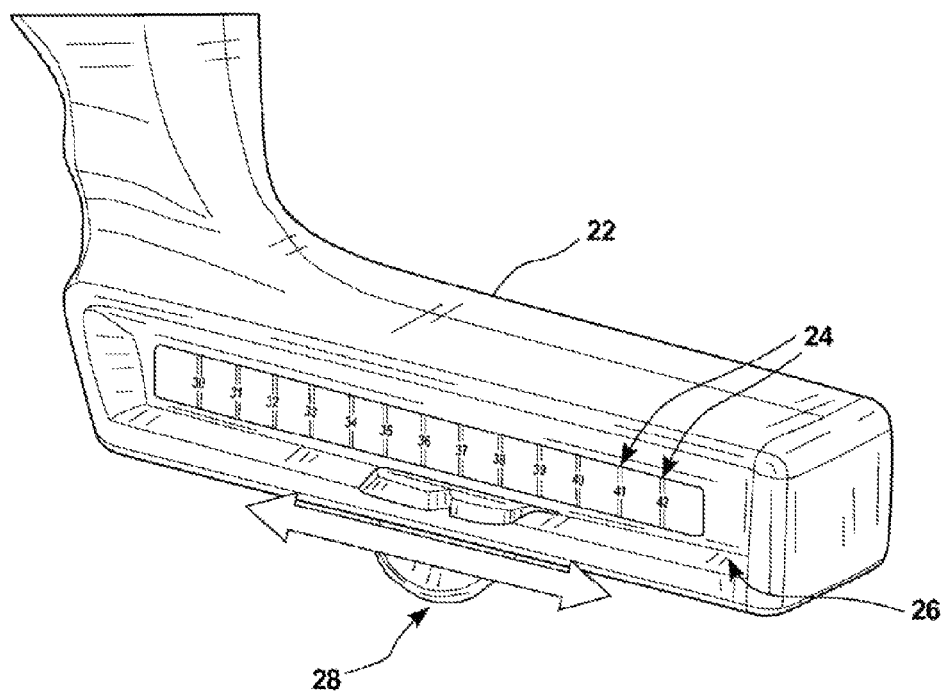
FIG. 4 is a close-up perspective view of a portion of the tibial bone cut alignment system from FIG. 1.

With reference now to FIG. 4, as a next step, light emitter 28 may be moved through slot 26 along horizontal extension 22 to align a midline of light emitter 28 with one of measurement indicators 24, based on the measured length of the tibia T. Measurement indicators 24 are numbered according to various tibial lengths in centimeters. (Inches may be used in an alternative embodiment.) When set to the correct length of the tibia T, handle is configured to provide a three degree (3°) tibial slope when the tibial bone cut is made. In alternative embodiments, horizontal extension 22 may have a different configuration and/or light emitter 28 may be coupled with handle 12 in a different way to allow adjustability for tibial length.

The steps just described may in some embodiments be performed in a slightly different order. For example, the tibia T may be measured and light emitter 28 positioned before cutting guide 16 is attached to handle 12. There may other instances in which the order or number of steps of the described method may be altered without changing the method's effectiveness. Thus, this description of one embodiment of a method of aligning a tibial bone cut should not be interpreted to restrict the scope of the invention as described in the claims of this application.

Figure 5:
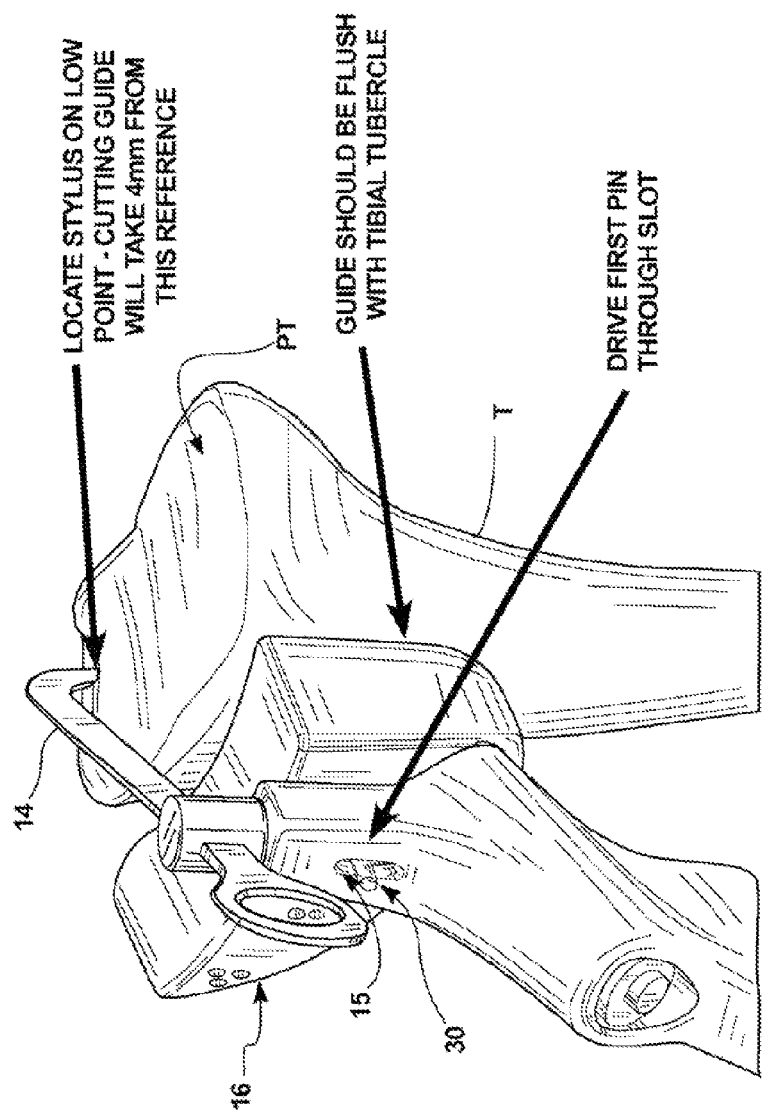
FIG. 5 is a close-up perspective view of a portion of the tibial bone cut alignment system from FIG. 1, coupled with a proximal end of a tibia.

Referring now to FIG. 5, the next step of the method may be to contact the end of stylus 14 with the low point (the lowest or most distal point) on the proximal surface of the tibia PT. This low point on the proximal surface PT acts as a reference point to allow system 10 to position cutting guide 16 at a desirable level for making the tibial bone cut. For example, in the embodiment shown, system 10 will position cutting guide 16 to make the bone cut approximately 4 mm below (distal to) the low point of the proximal tibial surface PT on which the end of stylus 14 rests. In alternative embodiments, a different cutting depth may be built into system 10 and/or cutting depth may be adjustable. In other alternative embodiments, stylus 14 may be replaced by any other suitable bone cut depth reference member, such as a post, bar, or the like.

Before, after, or at the same time as stylus 14 is contacted with the proximal tibia PT, cutting guide 16 may be positioned to contact the tibial tubercle. When stylus 14 has been positioned and cutting guide 16 is flush with the tibial tubercle, a first pin 30 may be advanced through slot 15 to attach cutting guide 16 to the tibia T.

Figure 6:
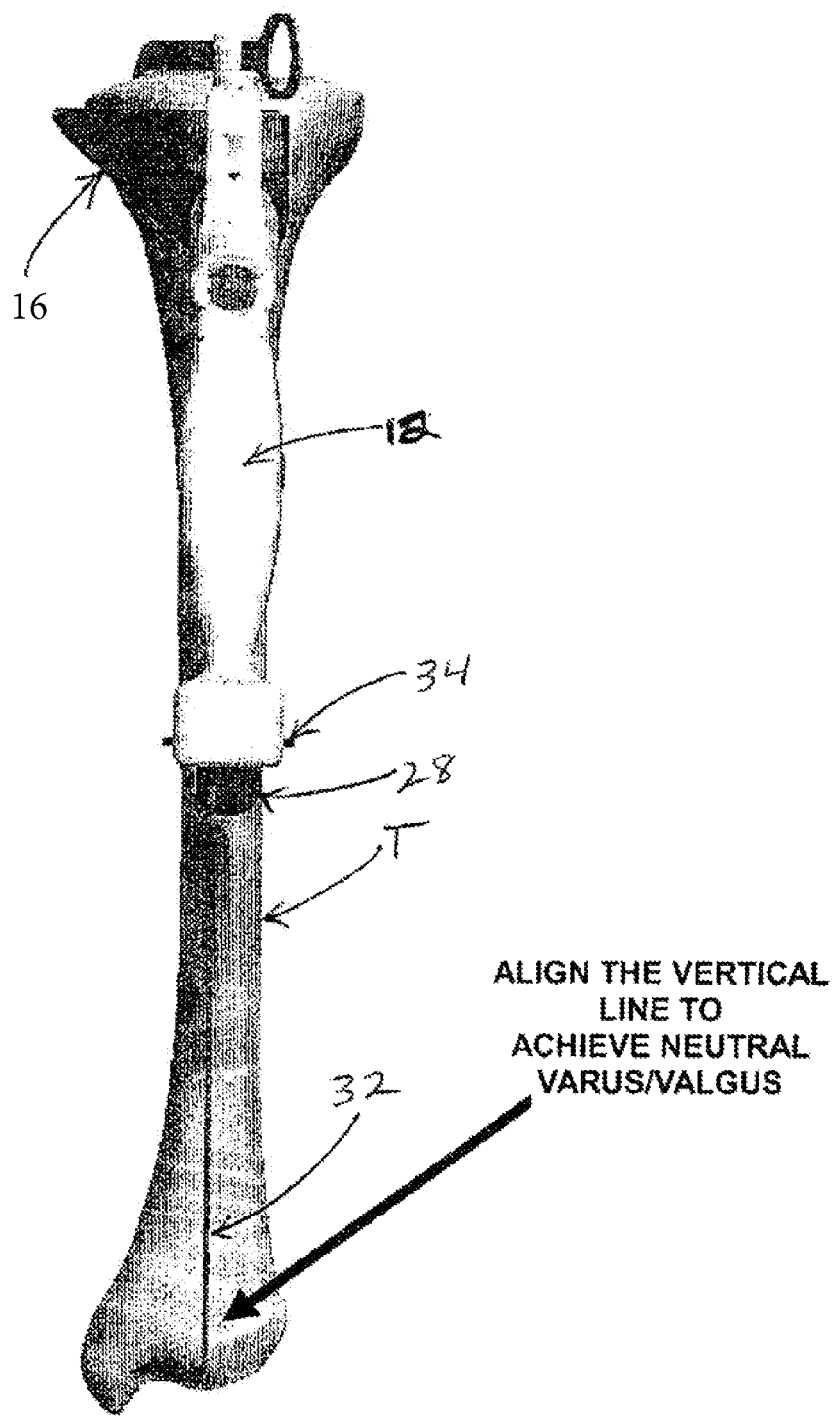
FIG. 6 is a front view of the tibial bone cut alignment system from FIG. 1, coupled with a tibia and emitting vertically and horizontally oriented laser lights.

Referring to FIG. 6, the next step may involve activating trigger switch 20 (not visible on FIG. 6) to activate laser light emitter 28. Light emitter 28 emits laser light in a vertically oriented line 32 and a horizontally oriented line 34, thus forming a cross-shaped light pattern along the tibia T. Handle 12 may be rotated left or right to align vertically oriented line 32 along approximately a midline of the tibia T to adjust the varus/valgus orientation of the bone cut. As handle 12 is rotated, cutting guide 16 moves with handle 12 (to which it is still locked) and thus moves relative to the tibia T. Thus, this step in the method adjust the varus/valgus angle of the bone cut that will be made using bone cutting guide 16.

Figure 7:
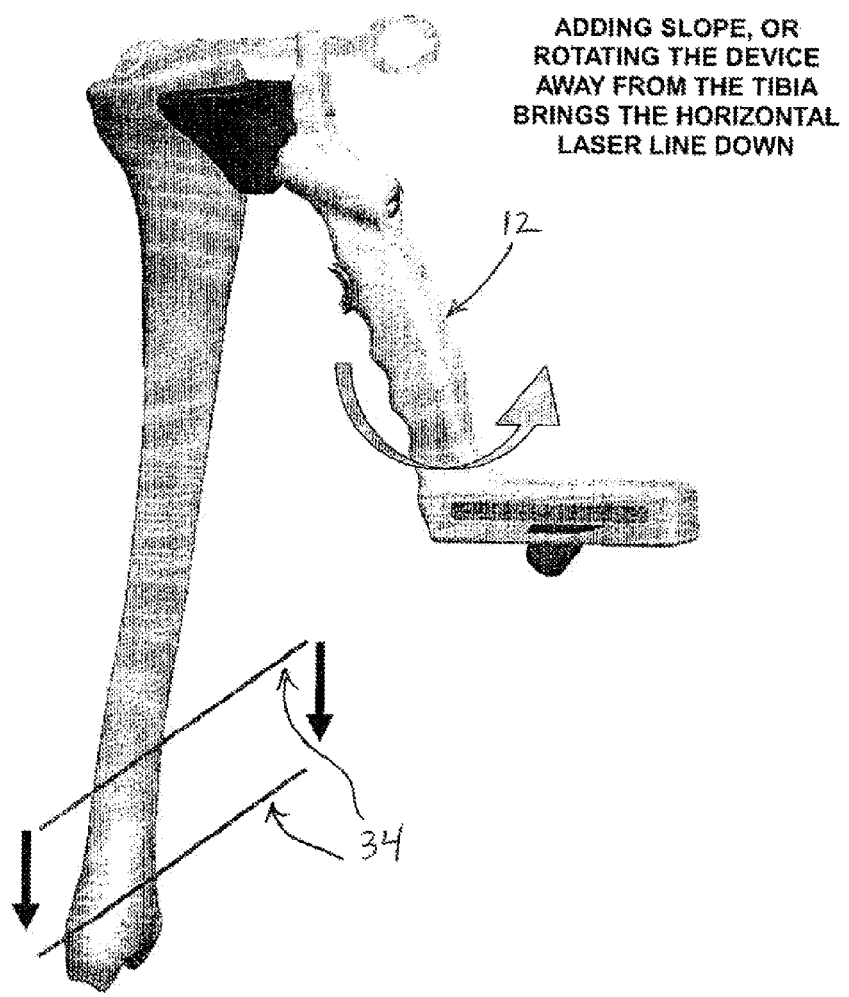
FIG. 7 is a perspective view of the tibial bone cut alignment system from FIG. 1, coupled with a tibia, demonstrating adjustment of the system to change the position of a horizontally oriented laser light.

Turning now to FIG. 7, once the varus/valgus angle is aligned, the tibial slope (anterior/posterior angle) is aligned by rotating handle away from or toward the tibia T to thus move horizontally oriented line 34 up or down the tibia T. Of course, tibial slope may be aligned before varus/valgus angle is aligned, depending on user preference, and adjustments to either or both may be made multiple times during the adjustment/alignment process.

Figure 8:
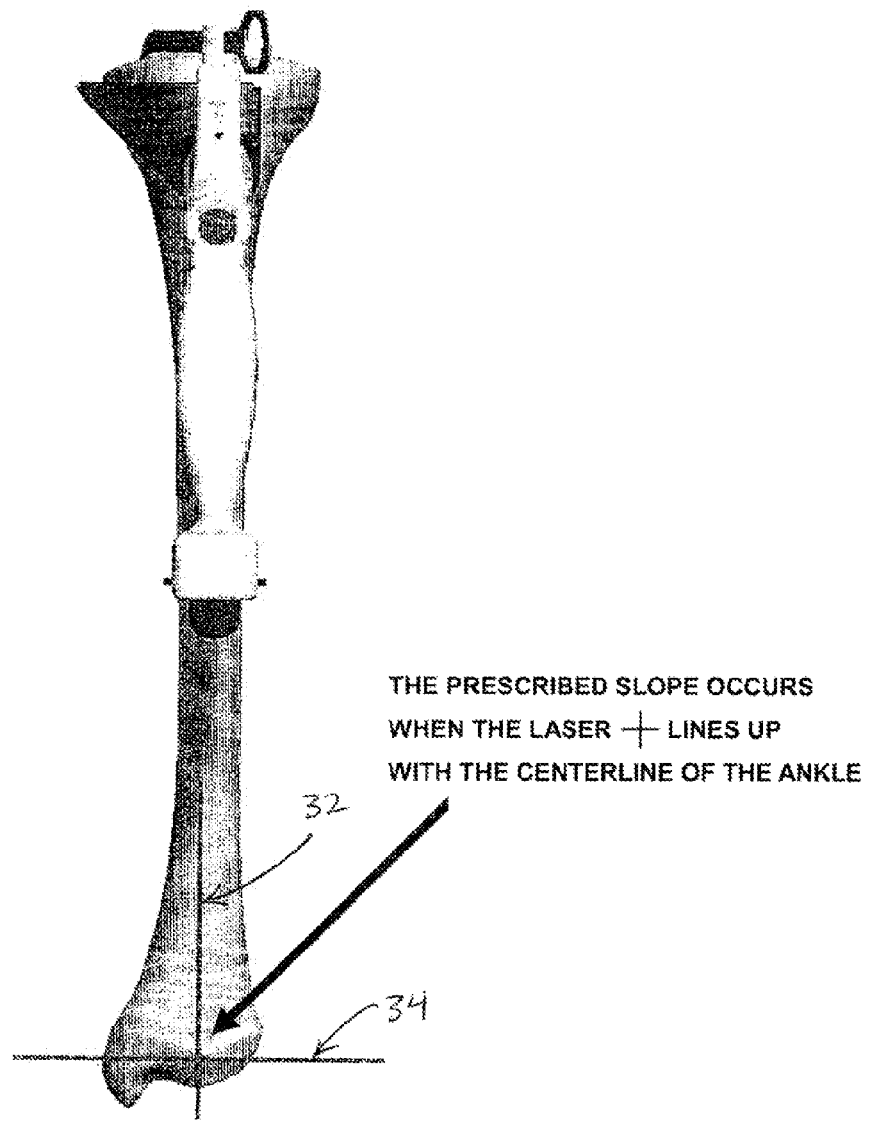
FIG. 8 is a front view of the tibial bone cut alignment system from FIG. 1, coupled with a tibia and emitting vertically and horizontally oriented laser lights, with the lights adjusted to a desired position for aligning the bone cutting guide.

As shown in FIG. 8, the cross-shaped laser light pattern emitted by emitter 28 may be adjusted until a desired position is reached. In the embodiment shown, the ideal position for the intersection of the crossed light lines 32, 34 is at the centerline of the ankle. Of course, in alternative embodiments system 10 may be configured to use a different tibial reference point for alignment of laser lights 32, 34.

Figure 9:
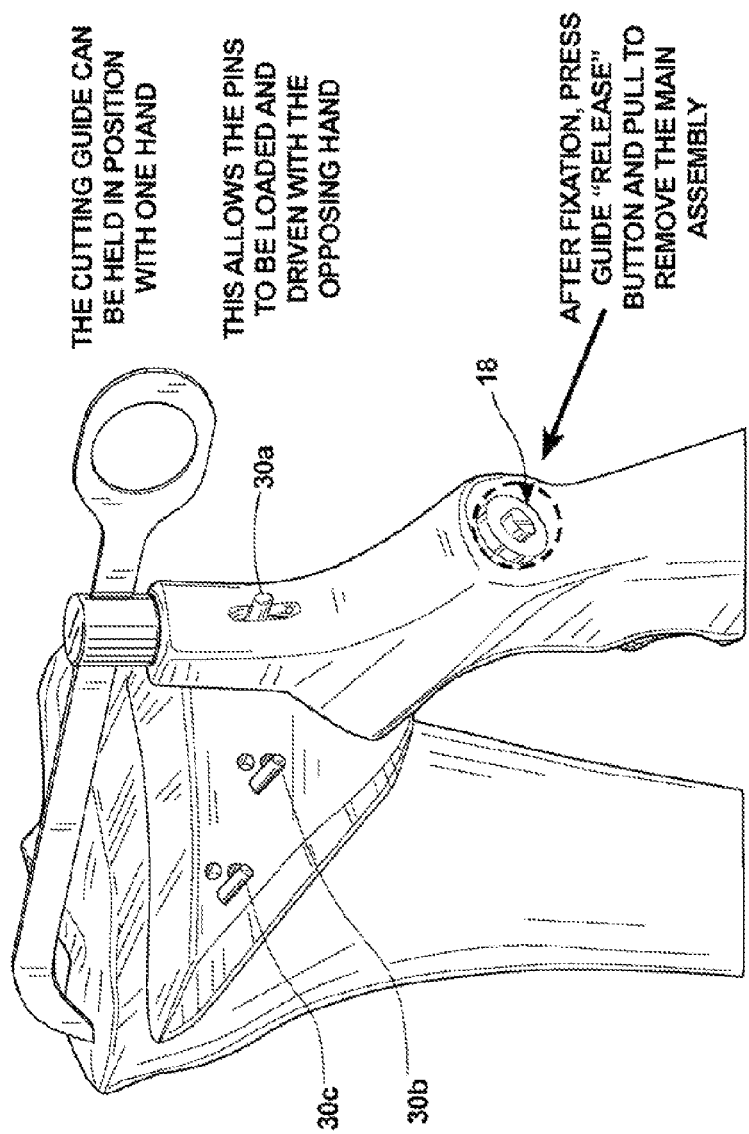
FIG. 9 is a close-up perspective view of a portion of the tibial bone cut alignment system from FIG. 1, coupled with the tibia and showing the final steps of a bone cutting guide alignment method.

Finally, referring now to FIG. 9, when laser lights are aligned to a desired location as shown previously, one or more additional pins 30*b*, 30*c* may be driven through cutting guide 16 to attach it securely to the tibia T. Whereas the first pin 30*a* attached guide 16 to the tibia T in such a way that it could continue to move/rotate relative to the tibia T and thus have its position adjusted by system 10, additional pins 30*b*, 30*c* attach cutting guide in an immobile way, so that it can no longer move relative to the tibia T and thus is secure when tibial bone cuts are made. One bone cutting guide 16 is securely fastened to the tibia T, guide release button 18 may be depressed, and handle 12 may be removed from cutting guide 16. Cutting guide 16 may then be used to guide a bone saw in making the tibial bone cut(s).

The present invention may be embodied in other specific forms without departing from the essential characteristics thereof. For example, in alternative embodiments method steps may be deleted, added or performed in a different order than that described above. In one embodiment, for example, it may be possible to perform the tibial slope (anterior/posterior) adjustment prior to the varus/valgus adjustment. Thus, the embodiments described above as well as alternative embodiments and equivalents are intended to be included within the scope of the present invention, which is set forth in the following claims.

The invention claimed is:

1. A method for positioning a bone cutting guide on a tibia, the method comprising:
    coupling the bone cutting guide with a cutting guide alignment device;
    measuring a length of the tibia from approximately a tibial plateau to a centerline of a malleolus of the tibia;
    adjusting the alignment device according to the length of the tibia;
    positioning a stylus of the alignment device on a low point of a proximal end of the tibia;
    contacting the cutting guide with a tibial tubercle of the tibia;
    driving a first pin through a first opening on the cutting guide into the tibia;
    adjusting the alignment device to align a laser light emitted from an adjustable laser light emitter portion of the alignment device approximately with a center of an ankle formed by the distal end of the tibia, wherein adjusting the alignment device includes sliding the laser light emitter along a horizontal extension on a distal end of the cutting guide alignment device within a slot in the horizontal extension; and
    driving at least a second pin through a second opening on the cutting guide into the tibia to secure the cutting guide to the tibia in the adjusted position.

2. A method as in claim 1, further comprising driving at least a third pin through a third opening on the cutting guide into the tibia.

3. A method as in claim 1, wherein coupling the bone cutting device with the alignment device comprises:
    pressing a guide release button on the alignment device;
    sliding the cutting guide onto a post on the alignment device; and
    releasing the guide release button to lock the cutting guide onto the alignment device.

4. A method as in claim 3, further comprising, after driving the second pin:
    pressing the guide release button; and
    removing the alignment device from the cutting guide, leaving the cutting guide attached to the tibia.

5. A method as in claim 1, wherein adjusting the alignment device according to the length of the tibia comprises adjusting a laser emitting member to direct the emitted laser light along the length of the tibia.

6. A method as in claim 1, wherein adjusting to align the emitted laser light comprises:
    aligning a vertically oriented laser light along approximately a midline of the tibia; and aligning a horizontally oriented laser light along approximately a centerline of the ankle.

7. A method as in claim 1, further comprising:
removing the alignment device from the cutting guide; and
cutting the tibia with a bone saw, using the attached cutting guide.

8. The method of claim 1, wherein sliding the laser light emitter along the slot includes using a plurality of measurement indicators along the horizontal extension to determine a corresponding tibial length.

9. A method for aligning a bone cutting guide on a tibia, the method comprising:
coupling a cutting guide alignment device and an attached cutting guide with a tibia;
adjusting a laser light emitter secured within a horizontal extension on a distal end of the cutting guide alignment device along a slot within the horizontal extension to account for a length of the tibia;
adjusting the alignment device in a varus/valgus orientation, using a vertically oriented laser light emitted from the laser light emitter portion of the alignment device;
adjusting the alignment device in an anterior/posterior orientation, using a horizontally oriented laser light emitted from the laser light emitter portion of the alignment device;
attaching the cutting guide to the tibia; and
removing the alignment device from the cutting guide, leaving the cutting guide attached to the tibia,
wherein adjusting the alignment device moves the cutting guide relative to the tibia.

10. A method as in claim 9, wherein adjusting the alignment device in the varus/valgus direction comprises rotating a handle of the device to the left and/or right, and wherein adjusting the alignment device in the anterior/posterior direction comprises rotating the handle toward and/or away from the tibia.

11. A method as in claim 9, wherein the attached cutting guide is configured to provide approximately a 3 degree tibial slope when attached according to the adjustments to the alignment device.

12. A method as in claim 9, further comprising, after removing the alignment device from the cutting guide, using a bone saw to make a cut on the tibia, using the cutting guide.

13. The method of claim 9, wherein adjusting the laser light emitter along the slot includes using a plurality of measurement indicators along the horizontal extension to determine a corresponding tibial length.

14. A device for positioning a bone cut on a tibia, the device comprising:
a handle;
an adjustable laser light emitter integrated into a horizontal extension from a distal portion of the handle and configured to be adjustable according to a length of the tibia, the laser light emitter slidable within a slot in the horizontal extension and configured to emit a cross-shaped pattern to guide varus/valgus angle and tibial slope adjustment for cutting guide placement in reference to the tibia;
a cutting guide attachment member integrated into the handle for removably attaching a cutting guide to the handle;
a guide release actuator, integrated into the handle, to disengage at least a portion of the cutting guide attachment member enabling attachment and removal of the cutting guide from the handle; and
a proximal tibia contacting member coupled to a proximal portion the handle for contacting a low point on a proximal end of the tibia as a reference point for the device.

15. A device as in claim 14, wherein the handle comprises:
a horizontal portion having a slot along which the laser light emitter slides.

16. A device as in claim 15, wherein the horizontal portion includes numbers denoting different lengths of tibias to facilitate adjustment of the laser light emitter.

17. A device as in claim 14, wherein the proximal tibia contacting member comprises a stylus.

18. A device as in claim 14, further comprising:
a left bone cutting guide for use in cutting a left tibia; and
a right bone cutting guide for use in cutting a right tibia.

19. The device of claim 14, wherein the adjustable laser light emitter includes a plurality of measurement indicators along the horizontal extension, the measurement indicators providing numerical indication of tibial lengths.

20. A system for positioning a bone cut on a tibia, the system comprising:
a handle;
an adjustable laser light emitter coupled with the handle and configured to be adjustable according to a length of the tibia, the adjustable laser light contained within a slot in a horizontal extension on a distal end of the handle to enable sliding adjustment within the slot along a length of the horizontal extension;
a cutting guide attachment member coupled with the handle;
a proximal tibia contacting member coupled with the handle for contacting a low point on a proximal end of the tibia as a reference point for the device; and
at least one bone cutting guide removably attachable to the handle via the cutting guide attachment member.

21. A system as in claim 20, wherein the handle comprises:
a cutting guide release actuator for releasing the cutting guide from the cutting guide attachment member.

22. A system as in claim 21, wherein the horizontal portion includes numbers denoting different lengths of tibias to facilitate adjustment of the laser light emitter.

23. A system as in claim 20, wherein the proximal tibia contacting member comprises a stylus.

24. A system as in claim 20, wherein the at least one bone cutting guide comprises:
a left bone cutting guide for use in cutting a left tibia; and
a right bone cutting guide for use in cutting a right tibia.

* * * * *